United States Patent [19]

Munson, Jr.

[11] 4,210,666
[45] Jul. 1, 1980

[54] MUCOLYTIC THIOPHENECARBOXAMIDO ALKYL MERCAPTANS

[75] Inventor: Harry R. Munson, Jr., Richmond, Va.

[73] Assignee: A. H. Robins Company, Incorporated, Richmond, Va.

[21] Appl. No.: 4,622

[22] Filed: Jan. 18, 1979

Related U.S. Application Data

[63] Continuation-in-part of Ser. No. 932,746, Aug. 10, 1978, abandoned.

[51] Int. Cl.² .................... A61K 31/38; C07D 333/02
[52] U.S. Cl. .................................................. 424/275
[58] Field of Search .................. 424/275; 260/332.2 C

[56] References Cited

U.S. PATENT DOCUMENTS

| | | | |
|---|---|---|---|
| 3,091,569 | 5/1963 | Sheffner | 424/319 |
| 3,344,153 | 9/1967 | Kühle et al. | 424/322 X |
| 3,663,690 | 5/1972 | Eichel et al. | 424/94 |
| 4,096,277 | 6/1978 | Martin | 424/324 |

OTHER PUBLICATIONS

Sheffner, Annals of N.Y. Acad. Sci. (1963) vol. 106, Article 2, pp. 298–301.

*Primary Examiner*—Leonard Schenkman

[57] ABSTRACT

2-Thiophenecarboxamido-alkylmercaptans having the formula

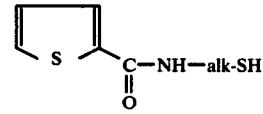

wherein alk is a straight or branched divalent alkylene radical of 2 to 4 carbon atoms and methods of using the compounds as mucolytic agents in combating lung mucus and compositions for use as mucolytic agents are disclosed.

7 Claims, No Drawings

MUCOLYTIC THIOPHENECARBOXAMIDO ALKYL MERCAPTANS

The present application is a continuation-in-part application of copending application Ser. No. 932,746 filed Aug. 10, 1978 now abandoned.

BACKGROUND OF THE INVENTION

1. Field of Invention

The present invention is concerned with certain mercaptans possessing mucolytic activity and is particularly concerned with certain 2-thiophenecarboxamido alkyl mercaptans, compositions thereof and methods for employing the mercaptans as mucolytic agents in controlling and combating mucus build-up in an amimal exhibiting or suffering from lung congestion.

2. Description of the Prior Art

A. L. Sheffner, Ann. N. Y. Acad. Sci. 106, 298–310 (1963) discloses sulfhydryl-containing compounds having mucolytic activity and established the use of mucin mucoprotein as a test media. None of the compounds disclosed by Sheffner were of the 2-thiophenecarboxamido alkyl mercaptan type. T. A. Martin et al. in the U.S. Pat. No. 4,005,222 disclose mucolytic anilido alkyl mercaptans.

Benzamidoethyl mercaptan is a known compound, A. A. Goldberg et al., J. Chem. Soc. 1948, 1919–26, but there has been no disclosure of mucolytic activity.

SUMMARY OF THE INVENTION

The compounds of the present invention are 2-thiophenecarboxamido alkyl mercaptans illustrated generally by the following formula:

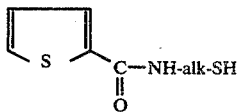

Formula I wherein alk is a straight or branched divalent alkylene radical of 2 to 4 carbon atoms.

The compounds have mucolytic activity and useful in dissolving and diluting mucus in warm-blodded animals exhibiting or suffering from lung congestions.

DESCRIPTION OF THE PREFERRED EMBODIMENTS

The compounds described hereinafter and represented by the foregoing Formula I have been shown by a modification of the method of S. J. Corne et al., J. Phys. 242, 116 (1974) as described hereinbelow to have mucolytic activity in animals.

Mucolytic activity for the compound 2-thiophenecarboxamidoalkylmercaptan was found to be of the same order of magnitude as N-acetyl-L-cysteine on rat stomach mucus and is therefore a preferred compound.

The method used to establish mucolytic activity in compounds of the present invention is as follows: Female Sprague-Dawley (Charles River Labs) 120–180 g. rats are fasted 16 hours on wire, housed two animals per cage. To minimize coprophagia, the lights are left on during the fast. Two cc. of water are given orally to each rat to minimize internal debris. Thirty minutes later the rats are sacrificed by cervical dislocation. The stomachs are removed, trimmed of excess tissue and the epithelial portion discarded. The glandular portion is cut sufficiently along the greater and lesser curvature to cause eversion of the stomach before placing it in the drug solution. Stomachs with a fecal odor or containing visible fecal matter are discarded. Stomachs are placed in 10 cc. of solution (50% PEG-300-H$_2$O) containing 2.5 mg. test compound/ml. for 40 minutes. After drug treatment the stomachs are placed in 10 cc. Alcian Blue (Solution 1) for 90 minutes where the dye complexes with the stomach mucus. After two successive 10-minute washes in 10 cc. of 0.25 M. sucrose (Solution 2), the stomachs are placed in 10 cc. of 0.5 MgCl$_2$ (Solution 3) for one hour to remove the complexed dye. The MgCl$_2$ supernatant is shaken with 10 cc. diethyl ether in a 60 cc. separatory funnel to remove lipids. The aqueous phase is drained into a Spectronic 20 Tube and the percent transmission is read at 605 m$\mu$ in a Spectronic 20 Spectrophotometer. The percent transmission is converted to $\mu$g/ml of Alcian Blue from a standard curve (P. Whiteman, Biochem. J. 131, 351–57 (1973). Each drug or drug vehicle (control) is tested on three stomachs. Mean differences between treated and control values are expressed as percentages.

Solution 1—Alcian Blue, 0.05% w/v (1 liter)

54.8 g. sucrose (0.15 M)
6.8 g. sodium acetate
900. cc. deionized water

Dissolve with a magnetic stirrer and adjust to pH 5.8 Add 500 mg. Alcian Blue 8GN (Matheson, Coleman & Bell #8E13). Fill to one liter in a volumetric flask. Refrigerate. Use only for one week.

Solution 2—Sucrose, 0.25 M (1 liter)

Add 85.6 g. of sucrose to 1 liter volumetric flask. Fill to volume with deionized water. Use only for one week.

Solution 3—Magnesium Chloride, 0.5 M (1 liter).

Add 101.7 g. MgCL$_2$·6H$_2$O (A.C.S.) to a one liter volumetric flask. Fill to volume with deionized water.

It is therefore an object of the present invention to provide certain novel 2-thiophenecarboxamidoalkyl mercaptans having mucolytic activity in a warm-blooded animal.

Another object is to provide a method of using 2-thiophenecarboxamidoalkyl mercaptans in combating mucus in an animal suffering from or exhibiting lung congestion.

A still further object is to provide novel pharmaceutical compositions for combating mucus in warm-blooded animals.

Additional objects and advantages of the present invention will be apparent to one skilled in the art and still others will become apparent from the following description of the best mode of carrying out the present invention and from the appended claims.

In the definition of the symbols and in Formula I given above and where they appear elsewhere throughout the claims and specification hereof, the term "alk" represents a selection from among ethylene (—CH$_2$CH$_2$—), propylene (—CH$_2$CH$_2$CH$_2$—),

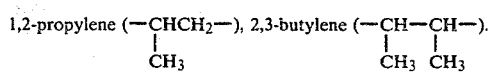

METHODS OF PREPARATION

The mercaptans of the present invention may be prepared by any one of three known methods as represented by the following equations; however, method (1) is preferred.

METHOD (1)  Via carbothioic acid ester acid salts

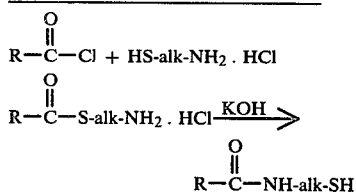

METHOD (2)  Via isothiouronium salts

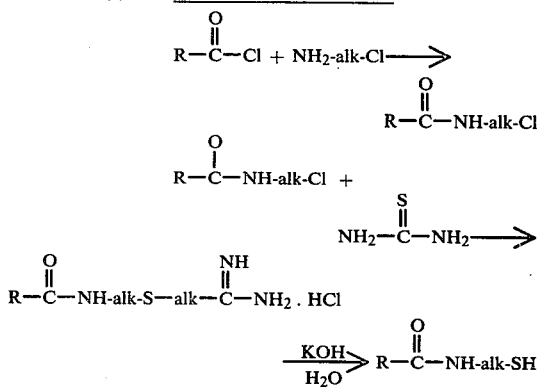

METHOD (3) R—COOH + HS-alk-NH$_2$ . HCl $\xrightarrow{\text{PCl}_3}{\text{Pyridine}}$ $$R-\underset{\underset{O}{\parallel}}{C}-\text{NH-alk-SH}$$

Preparation of intermediate esters obtained in Method (2) used to prepare compounds of the invention follow.

PREPARATION 1

2-Thiophenecarbothioic Acid, 2-Aminoethyl Ester, Hydrochloride.

A mixture of freshly distilled 2-thiophenecarbonyl chloride, 15.8 g. (0.108 mole) and 2-aminoethanethiol hydrochloride, 11.3 g. (0.1 mole) was heated (protected from moisture) over a steam jet for 6 hours. The solid crystalline mass produced was crushed and triturated with warm 60°–110° C. ligroine and filtered to collect the crystals. After two recrystallizations from anhydrous ethanol, the product 8.41 g. (75.5%) melted at 195°–196.5° C. NHR, MS and IR all supported the structure of the title compound.

Analysis: Calculated for C$_7$H$_{10}$ClNOS$_2$: C,37.58; H,4.51; N,6.26. Found: C,37.68; H,4,50; N,6.30.

PREPARATION 2

When in the procedure of Preparation 1, 2-aminoethanethiol hydrochloride is replaced by equal molar amounts of 3-amino-propanethiol hydrochloride, there is obtained thiophenecarbothioic acid, 3-aminopropyl ester hydrochloride.

The following examples of preparation of the compounds of the invention are only intended to illustrate the present invention and are not to be construed as limiting the invention in any respect.

EXAMPLE 1

2-Thiophenecarboxamido Ethyl Mercaptan

To a solution of sodium hydroxide, 4.1 g. (0.1 mole) in 200 ml. of oxygen-free water was added in one portion 2-thiophenecarbothioic acid, 2-aminoethyl ester monohydrochloride, 11.15 g. (0.05 mole). Nitrogen was bubbled through the suspension as the temperature was raised briefly to reflux. The resulting slightly turbid solution was then acidified and the resulting suspension extracted carefully with chloroform. The extracts were combined, dried, concentrated and diluted with 35°–60° C. petroleum ether. The crystalline solid was separated by filtration and recrystallized from benzene-petroleum ether. Yield was 4.58 g. (50%) of product melting at 101°–103.5° C.

Analysis: Calculated for C$_7$H$_9$NOS$_2$: C,44.89; H,4.84;N,7.48. Found: C,45.24; H,4.86; N,7.47.

EXAMPLE 2

When in the procedure of Example 1, 2-thiophenecarbothioic acid, 3-aminoethyl ester monohydrochloride is replaced by an equal molar amount of
2-thiophenecarbothioic acid-3-aminopropyl ester hydrochloride,
there is obtained
2-thiophenecarboxamido-propyl mercaptan.

The pharmaceutical compositions of this invention comprise compounds of Formula I above in an amount sufficient to provide effective mucolytic action against lung congestion in mammalian subjects when applied topically as an inhalant together with an acceptable carrier therefor.

The compounds of Formula I are administered in an amount sufficient to induce liquefaction of mucus in the respiratory tract of warm-blooded animals in need thereof. Intratracheal administration of the compounds of Formula I is affected by various inhalation or instillation means such as nose drops, sprays, aerosols, and the like. Examples of pharmaceutically acceptable liquid carriers are water and polyethyleneglycol 300. Another suitable means of administration is by insufflation of micronized particles or ultra-fine powder utilizing only the energy of the inspiratory action or by use of aerosol propellants. Generally, the amount of the compound in the inhalant compositions will vary from about 0.5 to 75 weight % depending on the type of carrier, i.e., liquid or solid. Solutions or suspensions having about 0.5 to 20% by weight, preferably 5–10 weight %, of the mucolytic agent of Formula I are suitable for application by spraying with an atomizer, nebulizer, aerosol and the like. Dusts containing about 25–75% or more active agent in micronized form are also suitable, about 50% being preferable. An example of a pharmaceutically acceptable solid diluent and carrier for the micronized powder is lactic acid.

It will be readily apparent to those skilled in the medical arts that the correct dosage of a compound to be employed with any particular mammalian subject is determined by the severity of the condition requiring mucolytic therapy, as well as the age, sex, weight and general physical condition of the subject. Individual doses ranging from 5-100 mg. for inhalation by man are suitable and may be required for the mucolytic effect.

The pharmaceutical compositions may take the form of dilutions of the micronized compounds in dusts or solutions and suspensions in liquids suitably dispensed for inhalation.

| A. Powder for Administration via Inhaler Device | |
|---|---|
| 2-Thiophenecarbothioic Acid, 2-Aminoethyl Ester, Hydrochloride, micronized | 2.5 g. |
| Lactose powder | 2.5 g. |

The powders are blended aseptically and filled into hard gelatin capsules each containing 50 mg. of the mixture. This is suitable for dispersion into the inspired breath by means of a breath-operated inhaler device containing means for rupture of the capsule wall prior to dosing.

Various modifications and equivalents will be apparent to one skilled in the art and may be made in the compounds, compositions and methods of the present invention without departing from the spirit and scope thereof, and it is therefore understood that the invention is to be limited only by the scope of the appended claims.

What is claimed is:

1. A method of combating mucus build-up in a living warm-blooded animal for the purpose of alleviating lung congestion in an animal suffering therefrom by administering through inhalation an amount of a compound effective for dissolving lung mucus causing the congestion having the formula:

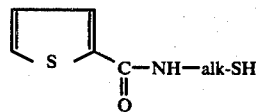

wherein -alk- is a straight or branched divalent alkylene radical of 2 to 4 carbon atoms.

2. The method of claim 1 wherein the compound is 2-thiophenecarboxamido-ethylmercaptan.

3. A pharmaceutical composition useful as a mucolytic agent in an animal body comprised of
   (a) 0.5 to 20% by weight of a compound of the formula:

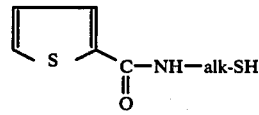

wherein -alk- is a straight or branched chain alkylene radical of 2 to 4 carbon atoms, and
   (b) a pharmaceutically acceptable liquid carrier therefor.

4. A composition of claim 3 wherein the compound is 2-thiophenecarboxamido-ethylmercaptan.

5. A compound of the formula

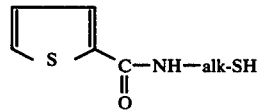

wherein -alk- is a straight or branched chain alkylene radical of 2 to 4 carbon atoms.

6. The compound of claim 5 which is 2-thiophenecarboxamido-ethylmercaptan.

7. A pharmaceutical composition in powder form, useful for insufflation as a mucolytic agent in an animal body comprised of
   (a) 25-75 weight % of a micronized compound of the formula

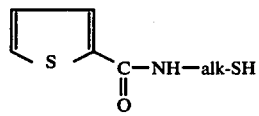

wherein -alk- is a straight or branched chain alkalene radical of 2 to 4 carbon atoms and
   (b) a pharmaceutically acceptable carrier therefor.

* * * * *